US010881578B2

(12) United States Patent
DeVore

(10) Patent No.: US 10,881,578 B2
(45) Date of Patent: Jan. 5, 2021

(54) TRACTION APPARATUS

(71) Applicant: Bryan DeVore, Snoqualmie, WA (US)

(72) Inventor: Bryan DeVore, Snoqualmie, WA (US)

(*) Notice: Subject to any disclaimer, the term of this patent is extended or adjusted under 35 U.S.C. 154(b) by 204 days.

(21) Appl. No.: 15/796,923

(22) Filed: Oct. 30, 2017

(65) Prior Publication Data
US 2019/0125624 A1 May 2, 2019

(51) Int. Cl.
A61H 19/00 (2006.01)
A61N 5/06 (2006.01)

(52) U.S. Cl.
CPC .......... *A61H 19/32* (2013.01); *A61N 5/0613* (2013.01); *A61H 2201/10* (2013.01); *A61H 2201/1207* (2013.01); *A61N 2005/0626* (2013.01); *A61N 2005/0645* (2013.01); *A61N 2005/0651* (2013.01); *A61N 2005/0659* (2013.01)

(58) Field of Classification Search
CPC . A61H 19/00–32; A61H 2201/10; A61F 5/41; A61F 2005/411–418; A61F 2/26; A61N 5/0613; A61N 2005/0632; A61N 2005/0635; A61N 2005/0645; A61N 2005/0659
See application file for complete search history.

(56) References Cited

U.S. PATENT DOCUMENTS

| | | | |
|---|---|---|---|
| 5,662,583 A | 9/1997 | Khouri | |
| 6,537,229 B1 | 3/2003 | Wang | |
| 8,126,558 B2 | 2/2012 | Forsell | |
| 8,944,993 B2 | 2/2015 | Forsell | |
| 9,610,214 B2 | 4/2017 | Zipper | |
| 9,655,724 B2 | 5/2017 | Forsell | |
| 9,662,117 B2 | 5/2017 | Forsell | |
| 9,662,213 B2 | 5/2017 | Forsell | |
| 2007/0179337 A1* | 8/2007 | Kalvatanond | A61F 5/41 600/38 |
| 2009/0024063 A1 | 1/2009 | Kalvatanond | |
| 2011/0172489 A1* | 7/2011 | Muller | A61F 5/41 600/39 |

(Continued)

FOREIGN PATENT DOCUMENTS

| | | |
|---|---|---|
| DE | 102009010220 B4 | 7/2011 |
| EP | 2510909 B1 | 9/2014 |
| WO | WO9706756 A1 | 2/1997 |

OTHER PUBLICATIONS

International Search Report and Written Opinion dated Jan. 19, 2019 in corresponding PCT international patent application No. PCT/US2018/054590, consisting of 7-pages.

*Primary Examiner* — Thaddeus B Cox
(74) *Attorney, Agent, or Firm* — David Postolski, Esq.; Gearhart Law LLC

(57) ABSTRACT

Disclosed embodiments provide a traction apparatus for promoting growth of a human penis. A light source is integrated with the traction apparatus for providing near infrared light to the penis and simultaneously apply a traction force. Embodiments include a base section, arm section, and head section. Magnetic mounts including electrical conductors supply electricity to the arm section and head section, providing power for a light source. The light source is configured to output light in near infrared wavelengths. The light can provide therapeutic effects that can enhance penis growth beyond that of a conventional traction device.

15 Claims, 21 Drawing Sheets

(56) References Cited

U.S. PATENT DOCUMENTS

| | | | |
|---|---|---|---|
| 2011/0270032 A1* | 11/2011 | Smith | A61F 5/41 600/38 |
| 2012/0005037 A1 | 1/2012 | Dodge | |
| 2013/0018221 A1 | 1/2013 | Ball | |
| 2016/0310353 A1* | 10/2016 | Barasch | A61H 19/00 |
| 2017/0281457 A1* | 10/2017 | Witt | A61H 9/0007 |

* cited by examiner

TRACTION APPARATUS

FIELD OF THE EMBODIMENTS

The field of the embodiments of this invention relates generally to traction devices and, more particularly, to an apparatus for applying traction to the human penis.

BACKGROUND OF THE EMBODIMENTS

Penis extenders involve using a penis traction device to stretch the penis. They can promote permanent penis enlargement and help to increase both penis length and girth (thickness). They may also help to treat erectile dysfunction and correct penile curvatures. The penis traction device works by applying constant traction force on the penis, which ultimately causes the cells of the penile tissue to multiply, and thus the penis grows bigger.

SUMMARY OF THE EMBODIMENTS

In one aspect, there is provided a traction apparatus for a penis, comprising: a base section; an arm section rotatably connected to the base section; a head section affixed to a distal end of the arm section; and a first light source affixed to the arm section, wherein the first light source is configured and disposed to provide light to the penis.

In another aspect, there is provide a traction apparatus where the arm section comprises a first arm and a second arm, and wherein the first arm comprises a first slide lock configured and disposed to extend the first arm, and wherein the second arm comprises a second slide lock configured and disposed to extend the second arm.

In another aspect, there is provided a traction apparatus where the head section comprises a second light source, wherein the second light source is configured and disposed to provide light to the penis.

In another aspect, there is provided a traction apparatus where the first light source and second light source comprise a plurality of light emitting diodes.

In another aspect, there is provided a traction apparatus where the first light source and second light source are both configured to emit light with a wavelength ranging from 630 nanometers to 980 nanometers.

In another aspect, there is provided a traction apparatus where the arm section comprises an arm magnetic mount on a distal end of the arm section, and wherein the head section comprises a head magnetic mount on an end of the head section.

In another aspect, there is provided a traction apparatus further comprising an extender section affixed to the head section.

In another aspect, there is provided a traction apparatus where the plurality of light emitting diodes that comprise the first light source and the second light source are configured in two rows.

In another aspect, there is provided a traction apparatus where a first row of light emitting diodes from the two rows of light emitting diodes is configured to emit light with a wavelength of 680 nanometers, and wherein a second row of light emitting diodes from the two rows of light emitting diodes is configured to emit light with a wavelength of 800 nanometers.

In another aspect, there is provided a traction apparatus for a penis, comprising: a base section; an arm section rotatably connected to the base section; a head section affixed to a distal end of the arm section; a first light source affixed to the arm section, wherein the first light source is configured and disposed to provide light to the penis; a controller coupled to the first light source, wherein the controller comprises: a processor; a communication interface coupled to the processor; a memory coupled to the processor; wherein the memory contains instructions, that when executed by the processor, perform the steps of: recording usage time; and transmitting the recorded usage time via the communication interface.

In another aspect, there is provided a traction apparatus where the arm section comprises a first arm and a second arm, and wherein the first arm comprises a first slide lock configured and disposed to extend the first arm, and wherein the second arm comprises a second slide lock configured and disposed to extend the second arm.

In another aspect, there is provided a traction apparatus where the head section comprises a second light source, wherein the second light source is configured and disposed to provide light to the penis.

In another aspect, there is provided a traction apparatus where the first light source and second light source comprise a plurality of light emitting diodes.

In another aspect, there is provided a traction apparatus where the first light source and second light source are both configured to emit light with a wavelength ranging from 630 nanometers to 980 nanometers.

In another aspect, there is provided a traction apparatus where the arm section comprises an arm magnetic mount on a distal end of the arm section, and wherein the head section comprises a head magnetic mount on an end of the head section.

In another aspect, there is provided a traction apparatus where the arm magnetic mount and the head magnetic mount each comprise an electrical conductor.

In another aspect, there is provided a method of elongating a penis, comprising: applying a traction force to the penis; and simultaneously applying light of one or more wavelengths to the penis while the traction force is being applied.

In another aspect, there is provided a method of elongating a penis where applying light of one or more wavelengths includes applying light of a wavelength ranging from 630 nanometers to 980 nanometers.

In another aspect, there is provided a method of elongating a penis comprising transmitting usage statistics to an external computing device.

In another aspect, there is provided a method of elongating a penis comprising transmitting a stop alert to an external computing device.

BRIEF DESCRIPTION OF THE DRAWINGS

The structure, operation, and advantages of disclosed embodiments will become further apparent upon consideration of the following description taken in conjunction with the accompanying figures (FIGS.). The figures are intended to be illustrative, not limiting. Certain elements in some of the figures may be omitted, or illustrated not-to-scale, for illustrative clarity.

DETAILED DESCRIPTION

Disclosed embodiments provide a traction apparatus for promoting growth of a human penis. A light source is integrated with the traction apparatus for providing near infrared light to the penis and simultaneously apply a traction force. Embodiments include a base section, arm section, and head section. Magnetic mounts including electrical conductors supply electricity to the arm section and head section, providing power for a light source. The light source is configured to output light in near infrared wavelengths. The light can provide therapeutic effects that can enhance penis growth beyond that of a conventional traction device.

Human bodies have cellular receptors for near infrared light. These cellular receptors, referred to as chromophores absorb specific wavelengths of near infrared light and use that energy for cellular action. When chromophores absorb near infrared light, they take that energy and use it to enhance the cell's production of adenosine triphosphate (ATP). ATP provides a mechanism for the human body to store chemical energy. The result of this energy is more cell power to produce proteins and heal tissue. In study after study, near infrared light makes the body repair itself faster and more efficiently. Near infrared light also enhances the cells' production of nitric oxide. Nitric oxide is a signal molecule that regulates vasodilation. The result of near infrared stimulation is increased levels of nitric oxide and enhanced circulation. Also, an added benefit is that increased nitric oxide confers anti-oxidant protection inside the cells. Furthermore, deoxyribonucleic acid (DNA) synthesis in fibroblasts and muscle cells has been quintupled by NASA using light emitting diode (LED) light alone, in a single application combining 680, 730 and 880 nanometer wavelengths each at 4 Joules per centimeter squared. Disclosed embodiments combine penis traction with infrared light, thereby reducing the time required in order to see noticeable improvement, and enabling a higher success rate for traction apparatus users.

Figure 1:
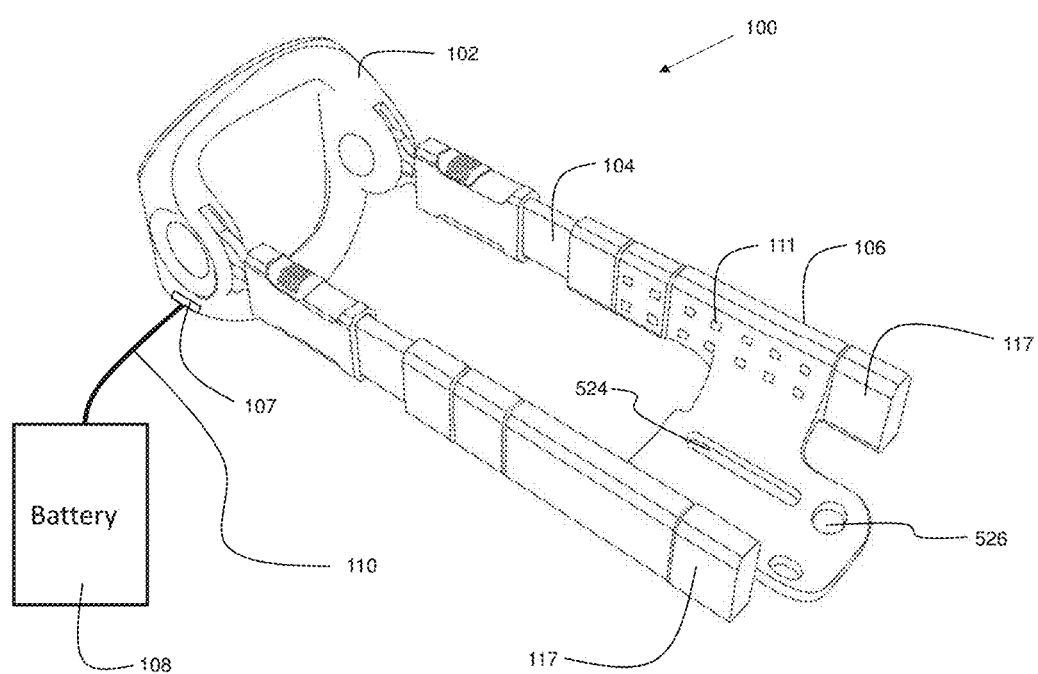
FIG. 1 shows a traction apparatus in accordance with embodiments of the present invention.

FIG. 1 shows a traction apparatus 100 in accordance with embodiments of the present invention. Traction apparatus 100 includes a base section 102, an arm section 104 that is rotatably connected to the base section 102, and a head section 106 affixed to a distal end of the arm section 104. In embodiments, an extender section 117 is affixed to the head section 106.

A battery 108 provides power via power connector cable 110 to a base power connector 107. In embodiments, the battery 108 is a thin battery that may be attached to the inside of the user's pants via a clip, hook-and-loop fastener, or other suitable mechanism. Disclosed embodiments may utilize a rechargeable battery, such as a lithium ion battery, or other suitable battery technology. A light source 111 is configured within the traction apparatus to provide light to the penis. In particular, the light source 111 is configured to provide near infrared (NIR) light wavelengths, ranging from 630 nanometers to 980 nanometers. Light of this wavelength range, in conjunction with a simultaneously applied traction force, can further enhance penis growth beyond that of a conventional traction device. In embodiments, the arm section 104, head section 106, and extender section 117 each have a light source (indicated generally as 111). In this way, light is applied to both the shaft and head of a penis during use. The head section 106 comprises a plurality of strap openings 524 and 526 to enable a strap to be threaded therethrough in order to secure the penis to the traction apparatus. Thus, in embodiments, the head section comprises a second light source, wherein the second light source is configured and disposed to provide light to the penis. In embodiments, the first light source and second light source comprise a plurality of light emitting diodes. In embodiments, the first light source and second light source are both configured to emit light with a wavelength ranging from 630 nanometers to 980 nanometers.

Figure 2:
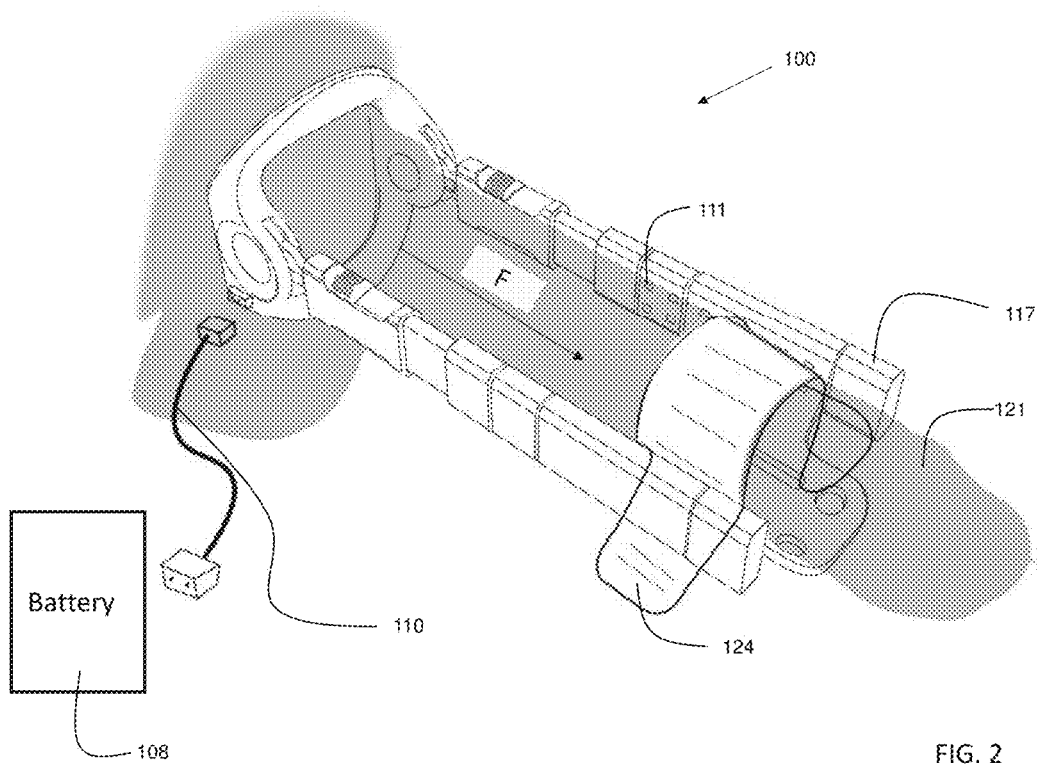
FIG. 2 shows an exemplary usage of an embodiment of the present invention.

FIG. 2 shows an exemplary usage of the embodiment shown in FIG. 1. A penis 121 is placed in the traction apparatus 100 as shown. A strap 124 secures the penis to the head section of the traction apparatus. The penis is thus pulled, applying a force in the direction indicated by arrow F. The light source 111 provides NIR light to the penis while it is under traction from the traction device to promote additional growth.

Figure 3A:
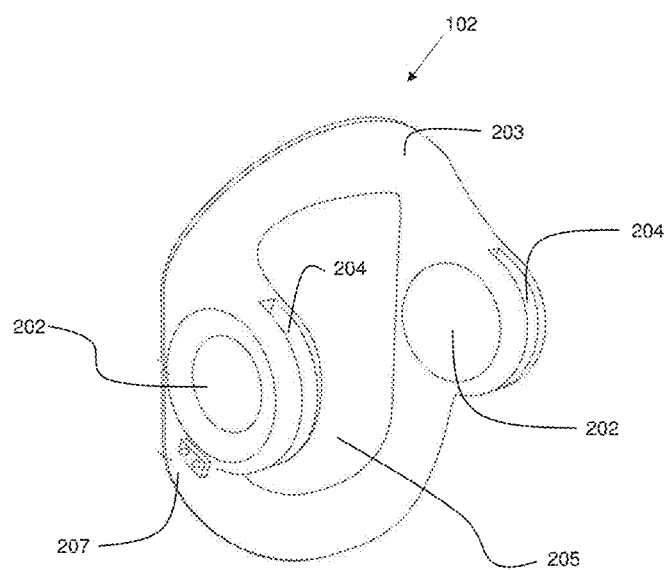
FIGS. 3A-3C show detail of a base section of embodiments of the present invention.
Figure 3B:
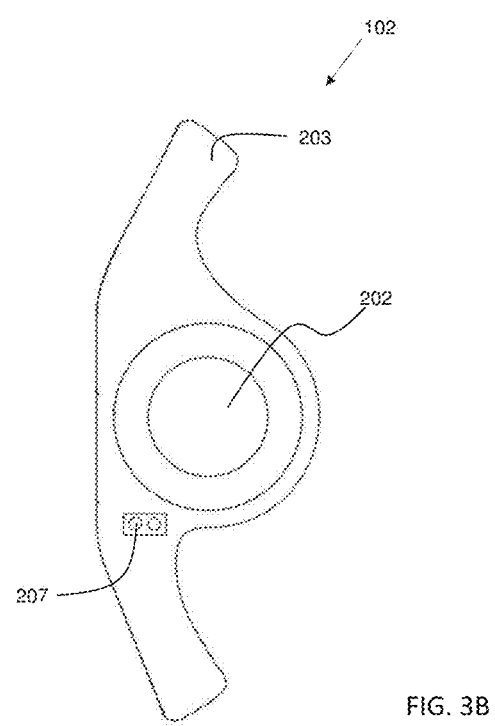
Figure 3C:
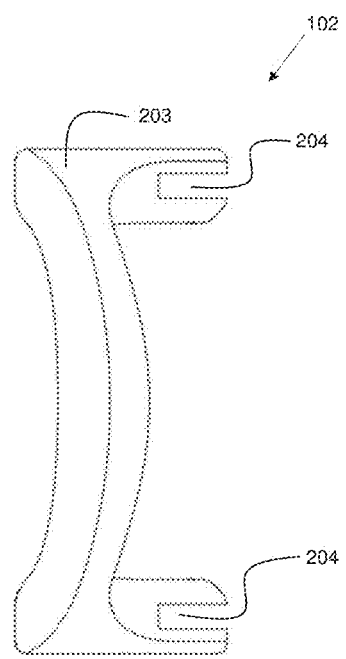

FIGS. 3A-3C show detail of a base section of embodiments of the present invention. FIG. 3A is a perspective view. FIG. 3B is a side view. FIG. 3C is a top-down view. The base section 102 comprises an annular bracket 203 which includes an opening 205 for a penis to go through. Thus, the bracket 203 of the base section 102 is proximal to the torso of a user during use. His penis traverses the opening 205. The arm section (104 of FIG. 1) attaches to the base section 102 through arm slits 204, and rotatably attaches to arm joints 202. The arm joints 202 allow the arm section 104 to rotate to different angles, allowing the traction apparatus to be comfortably worn, and be discrete under clothing. A main power connection 207 is configured to receive power from an external battery. In embodiments, the main power connection 207 may be a magnetic power connection.

Figure 4A:
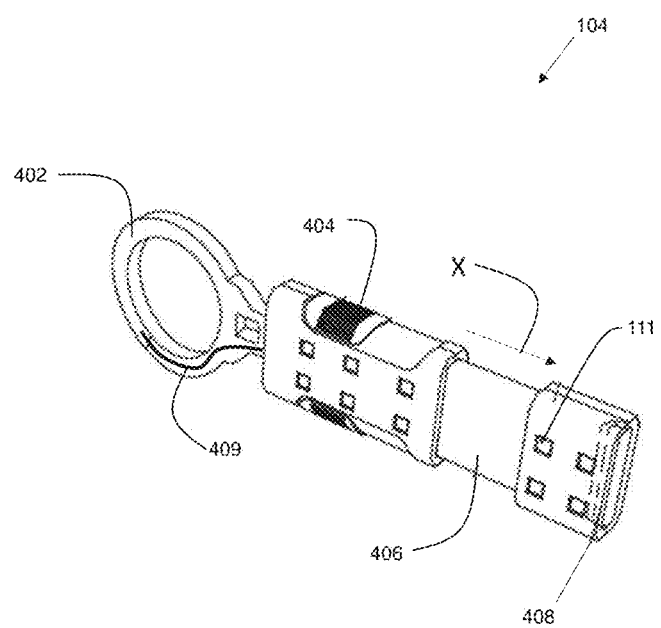
FIGS. 4A-4D show detail of an arm section of embodiments of the present invention.
Figure 4B:
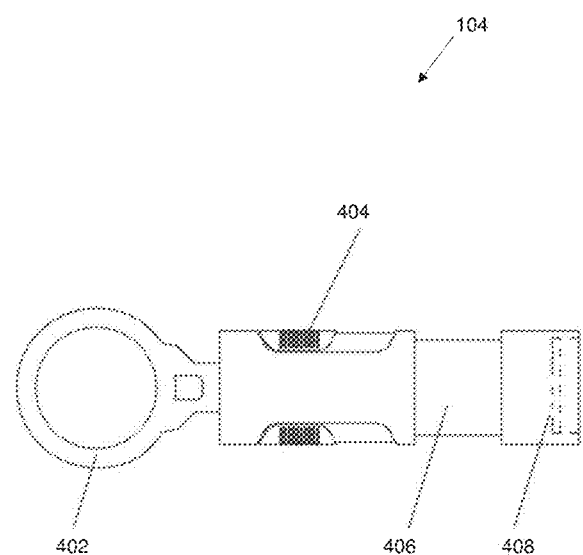
Figure 4C:
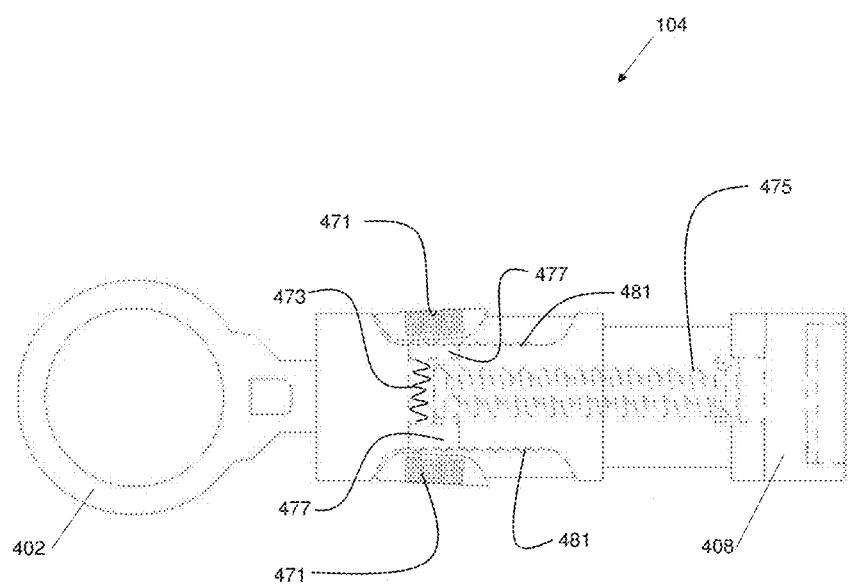
Figure 4D:
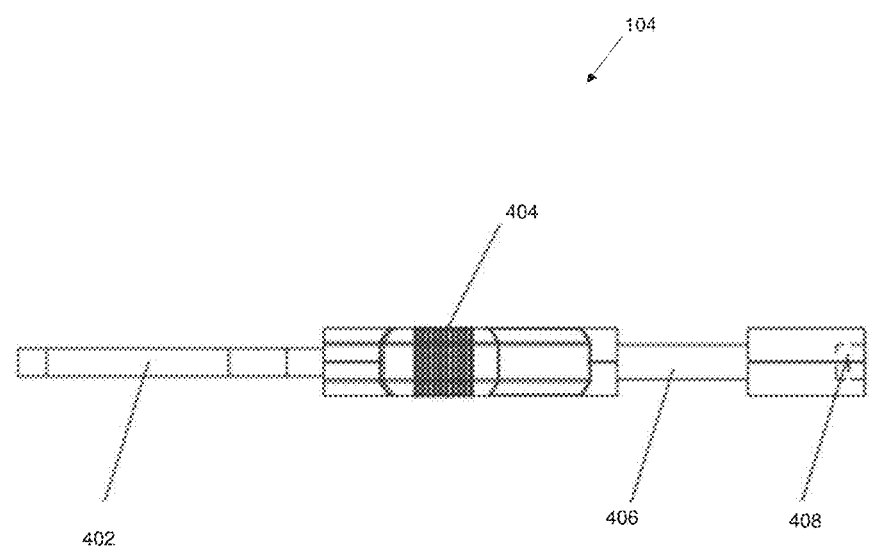

FIGS. 4A-4D show detail of an arm section of embodiments of the present invention. FIG. 4A is a perspective view. FIG. 4B is a side view. FIG. 4C is a cutaway view of the sideview shown in FIG. 4B. FIG. 4D is a top-down view. Arm section 104 comprises two arms. Referring to FIG. 4A, one of the two arms is shown in detail. The arm includes a pivot ring 402. The pivot ring 402 inserts into an arm slit 204 (FIG. 3A) of the base section. The pivot ring 402 has a conductive strip 409 to provide electricity from the base section to the arm section. The arm section 104 further comprises a slide lock 404. The slide lock provides a mechanism to adjust the length of the arm section along the direction indicated by arrow X. This allows the compression slider 406 of the arm section 104 to be extended in an adjustable manner to allow the traction apparatus to accommodate penises of various lengths.

Referring to FIG. 4C, a cutaway side view is shown. To extend the apparatus, a user can push on grips 471, which compress resilient member 473, and move brakes 477 away from respective corrugated ridges 481, allowing spring 475 to push the distal end of the arm, including magnetic power connection 408, to extend the arm section 104 to a desired length. The user then releases the grips 471, and the resilient member 473, which is mechanically coupled to brakes 477, presses the brakes 471 against corrugated ridges 481 to lock the arm section 104 in place.

At a distal end of the arm section 104 is a magnetic power connection 408. The magnetic power connection provides a mechanism to both attach, and provide power to, the head section of the traction apparatus. In embodiments, the arm section comprises a first arm and a second arm, and the first arm comprises a first slide lock configured and disposed to extend the first arm, and the second arm comprises a second slide lock configured and disposed to extend the second arm. The slide lock includes springs to create the desired amount of tension, compressing the springs, then locking the slide into place so that as the penis stretches, it is kept under tension until it reaches a point that the slide needs to be moved forward to create tension again.

Figure 4E:
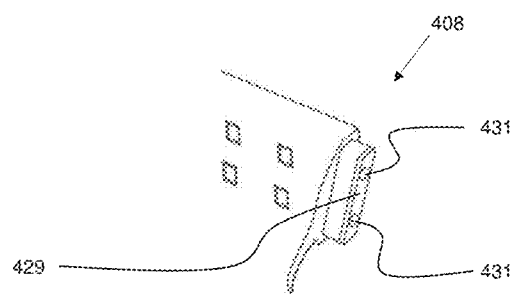
FIG. 4E shows details of a magnetic power connector.

FIG. 4E shows details of a magnetic power connection. A magnetic surface 429 is exposed on the magnetic power connection. A plurality of conductors, indicated generally as 431, traverse the magnetic surface. When a corresponding magnetic power connection is placed adjacent to the magnetic power connection of FIG. 4D, the magnetic surface 429 secures the two magnetic power connections together, while the conductors 431 align with conductors of the corresponding magnetic power connection to provide power to another section of the traction apparatus.

Figure 4F:
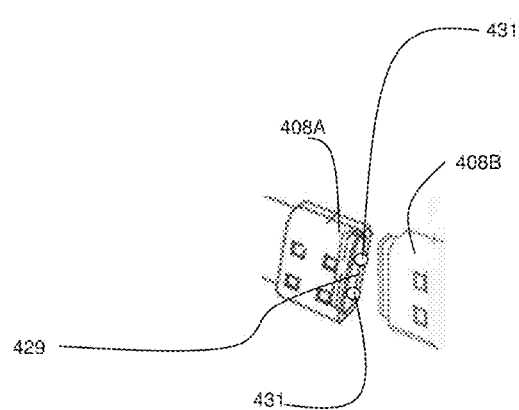
FIG. 4F shows connection of magnetic power connectors.

FIG. 4F shows connection of magnetic power connectors. Magnetic power connector 408A corresponds to arm section 104 (FIG. 1). Magnetic power connector 408B corresponds to head section 106 (FIG. 1). When the magnetic power connector 408A is placed adjacent to the magnetic power connector 408B, the magnetic surface 429 of each connector secures them together, while the conductors 431 of each connector align to provide power from connector 408A to connector 408B. This mechanism provides a convenient and safe way to provide power to the various sections of the traction apparatus, while allowing easy disassembling for storage. In embodiments, the arm magnetic mount and the head magnetic mount each comprise an electrical conductor. In embodiments, the arm magnetic mount and the head magnetic mount each utilize an opposite polarity magnetic surface, allowing the two connectors to magnetically couple upon contact with each other.

Figure 5A:
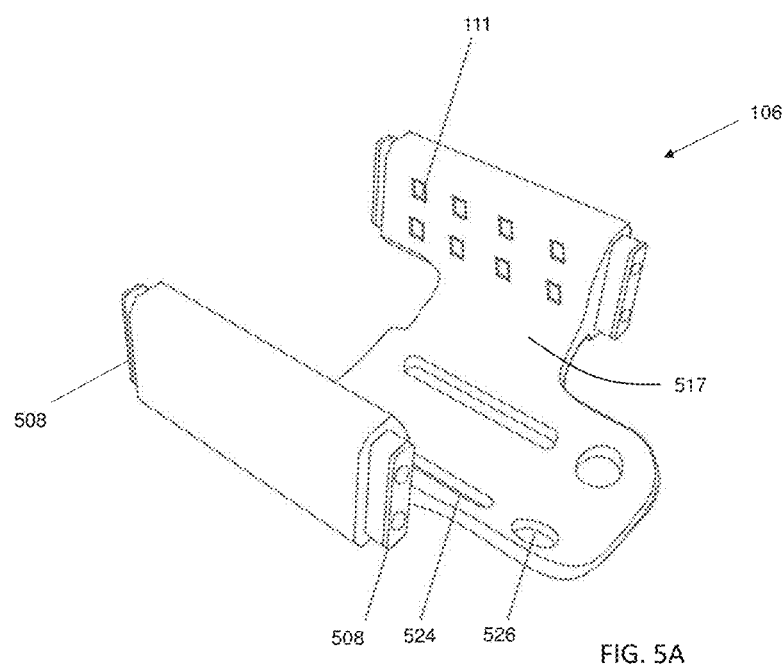
FIGS. 5A-5C show detail of a head section of embodiments of the present invention.
Figure 5B:
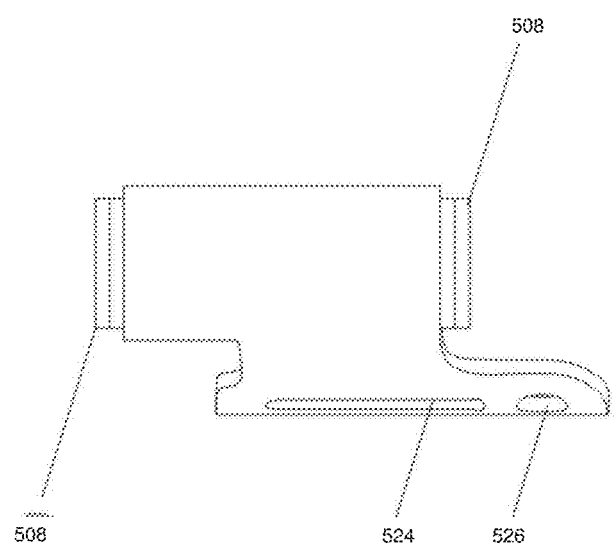
Figure 5C:
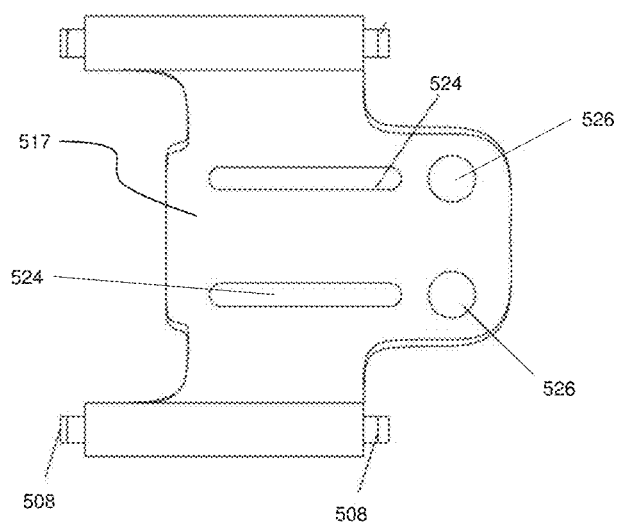

FIGS. 5A-5C show detail of a head section of embodiments of the present invention. FIG. 5A is a perspective view. FIG. 5B is a side view. FIG. 5C is a top-down view. Head section 106 comprises magnetic power connectors 508 for receiving power from the arm section 104 (FIG. 1) and supplying power to the extender section 117 (FIG. 1). A plurality of elongated strap openings 524 and a plurality of round strap openings 526 are formed in the bracket portion 517 of the head section 106. The strap openings 524 and/or 526 may be used to thread a strap through the openings and around the penis of a user to secure the penis to the head section.

Figure 6A:
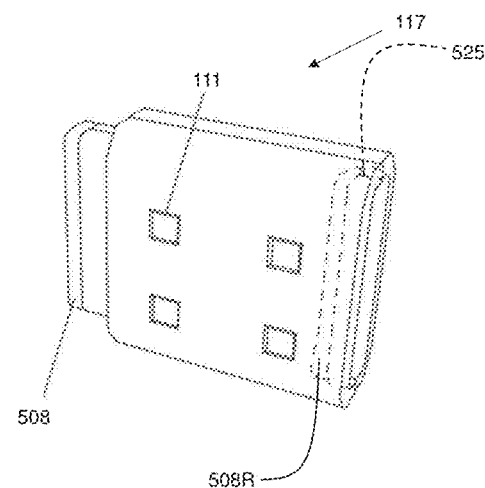
FIGS. 6A-6C show detail of an extender section of embodiments of the present invention.
Figure 6B:
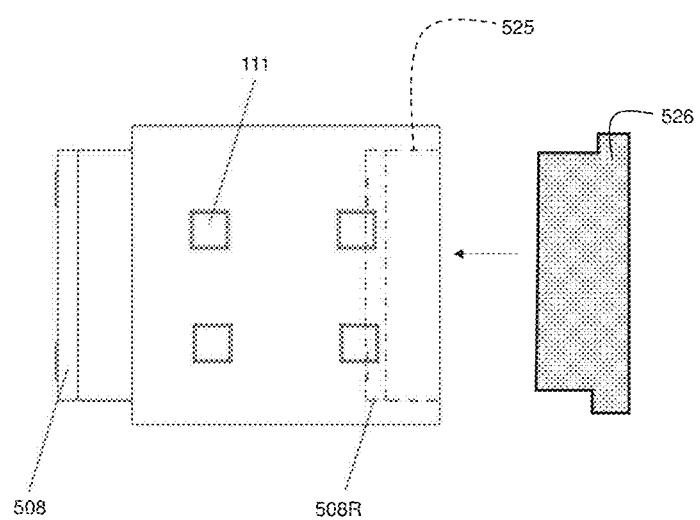
Figure 6C:
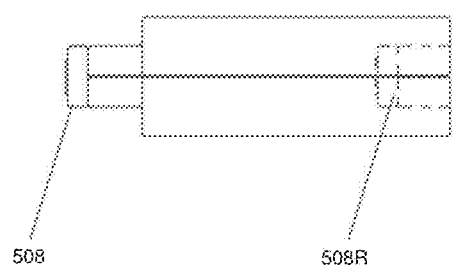

FIGS. 6A-6C show detail of an extender section 117 of embodiments of the present invention. Extender section 117 includes a magnetic power connection 508 which may be affixed to the head section 106. Extender section 117 further includes a recessed magnetic power connection 508R on an opposite end. The recessed magnetic power connection 508R allows multiple extender connections to be chained together to enable an additional length of the traction apparatus if needed. The recessed magnetic power connection 508R also serves as a way to safely terminate the power connection. In some embodiments, an insulating termination plug 526 (FIG. 6B) may be inserted in the cavity 525 of the recessed power connection 508R to further insulate the power connection. In embodiments, the insulating termination plug 526 may be comprised of plastic, or other suitable insulating material.

Figure 7:
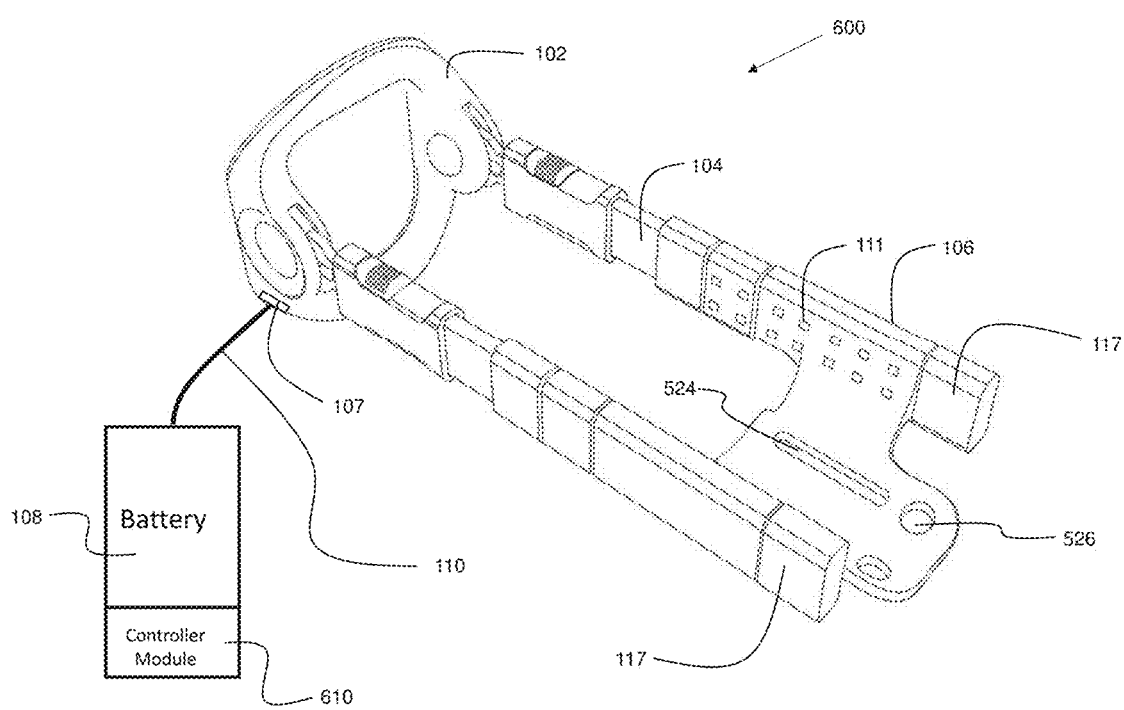
FIG. 7 shows a traction apparatus in accordance with additional embodiments of the present invention.

FIG. 7 shows a traction apparatus 600 in accordance with additional embodiments of the present invention. Traction apparatus 600 is similar to traction apparatus 100 of FIG. 1, with the main differences being the addition of a controller module 610. The controller module may include a processor to implement intelligent functionality into the traction apparatus 600. This intelligent functionality includes, but is not limited to, providing usage statistics to a user via an application (app) on a mobile computing device, and/or providing a stop alert when the user has worn the device for a predetermined amount of time. The stop alert is an indication for the user to stop using the device. The functionality may further include a feature of automatically disabling the light source(s) on the traction device after a predetermined amount of time. The functionality may further include activating and deactivating light sources of various wavelengths at a predetermined time to provide a range of different wavelengths of light that are provided to the penis.

As shown in FIG. 7, a light source may include a plurality of rows of LEDs. In embodiments, there is a first row of LEDs 511A, and a second row of LEDs 511B. In embodiments, the first row of LEDs 511A and the second row of LEDs 511B may be configured to emit light of the same wavelength. In embodiments, the first row of LEDs 511A and the second row of LEDs 511B may be configured to emit light of a different wavelength. For example, the first row of LEDs 511A may be configured to emit light with a wavelength of 680 nanometers, and the second row of light emitting diodes 511B may be configured to emit light with a wavelength of 800 nanometers. Other wavelength combinations are possible.

Figure 8A:
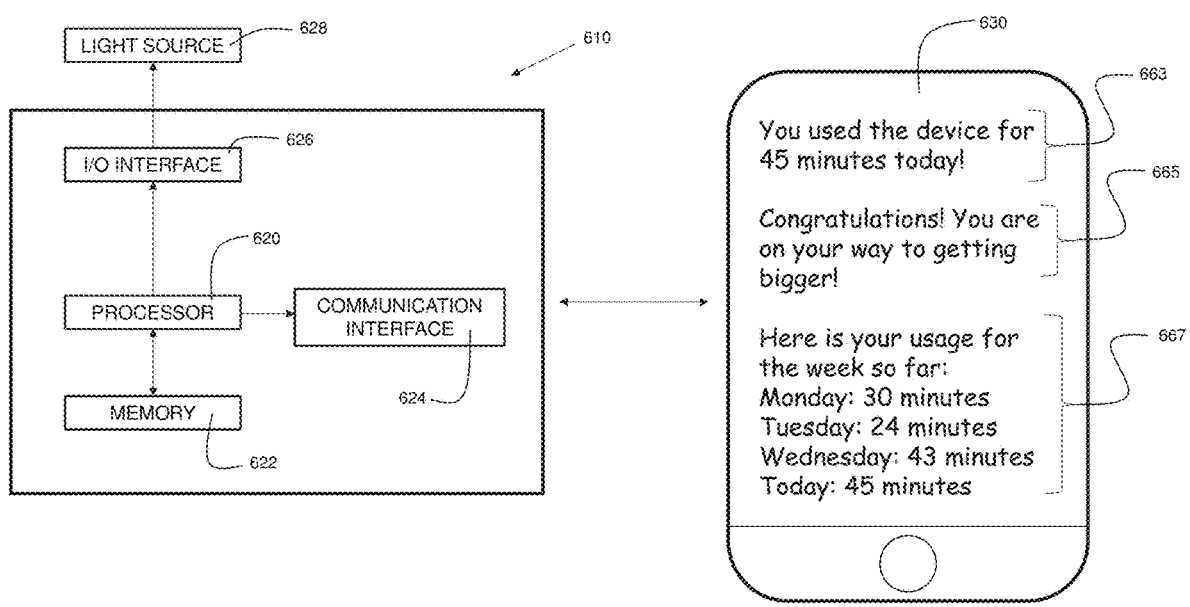
FIGS. 8A and 8B show exemplary usages of the embodiment of FIG. 7.
Figure 8B:
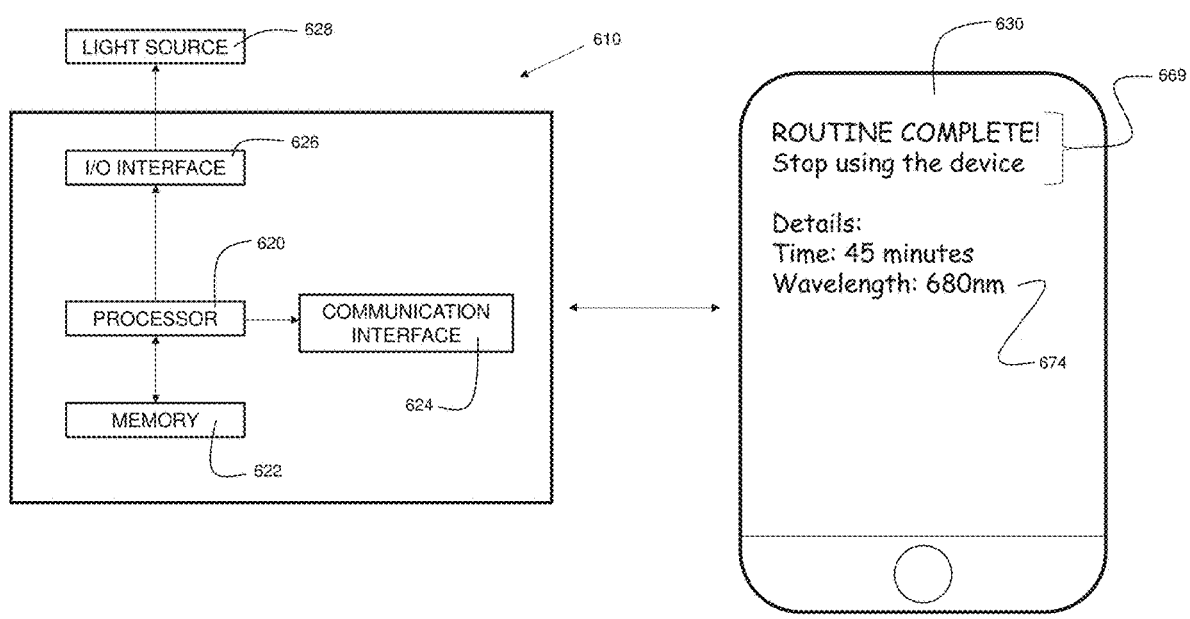

FIGS. 8A and 8B show exemplary usages of the embodiment of FIG. 7. The controller module 610 is shown in additional detail. The controller module 610 includes a processor 620. The controller module 610 further includes a memory 622 coupled to the processor. The memory 622 may include flash, read-only memory (ROM), static random-access memory (SRAM), and/or other suitable memory technology. In embodiments, the memory is a non-transitory computer-readable medium. The memory 622 contains instructions, that when executed by the processor 620, perform various steps in accordance with disclosed embodiments.

The controller module 610 further includes a communication interface 624. In embodiments, the communication interface 624 may include a wired interface, such as USB, or another serial interface. In embodiments, the communication interface 624 may include a wireless communication interface such as Bluetooth™ or Bluetooth Low Energy (BLE), to enable wireless communication with a mobile device such as a smartphone or tablet computer. The controller module 610 may further include an input/output (I/O) interface 626 for controlling the activation and deactivation of the light source 628 of the traction apparatus.

In embodiments, a corresponding application (app) is installed on a computing device 630. In embodiments, computing device 630 is a smartphone or tablet computer. In embodiments, the application executing on the computing device 630 queries the controller module 610 to retrieve usage information. The usage information can include usage time 663 and/or usage history 667, along with motivational messages 665 for the user, as shown in FIG. 8A.

FIG. 8B shows an example of communication initiated from the controller module 610 to the computing device 630. In embodiments, the processor 620 keeps track of usage time. When the usage time exceeds a predetermined duration (e.g. 45 minutes), the controller module 610 provides a stop alert 669 which is transmitted to the computing device 630. This can discretely remind the user that it is time to stop using the apparatus. Additionally, the controller module 610 may automatically deactivate the light source once the predetermined duration has been reached by controlling one or more signals of the I/O interface 626. The information transmitted by the controller module 610 may further include the wavelength(s) used during a usage session 674. In embodiments, the application on the computing device 630 may be used to establish desired usage times, wavelengths of light to be used, and other user preferences. These preferences may be communicated to the controller module 610 from the computing device 630 via communication interface 624.

Figure 9:
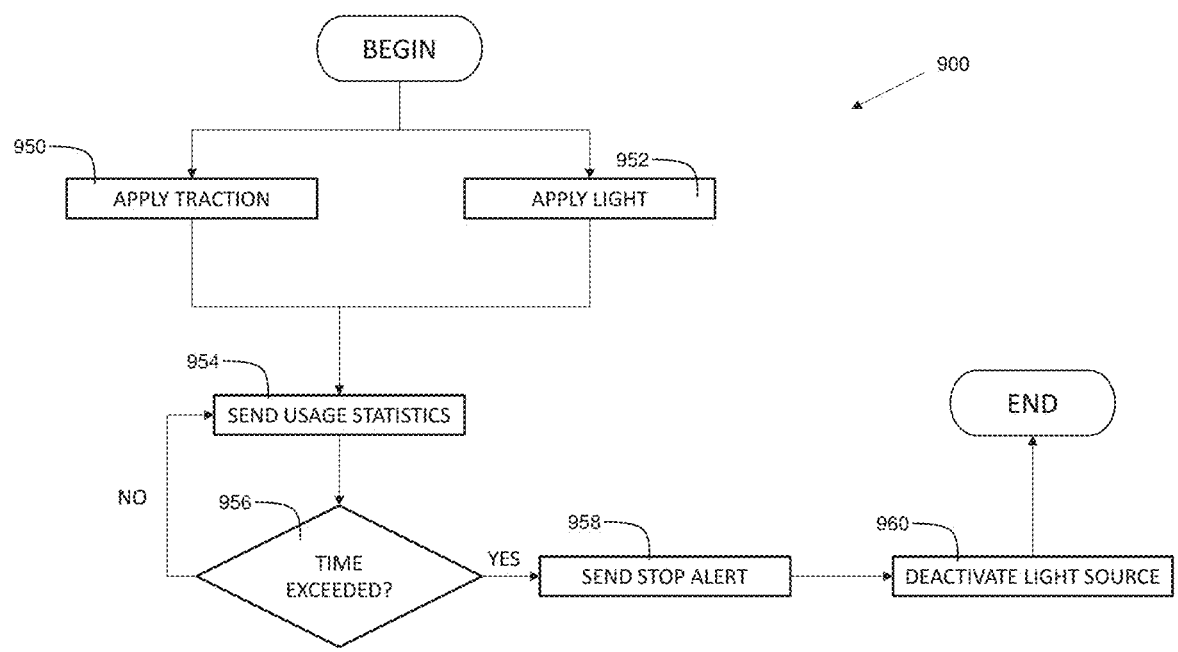
FIG. 9 is a flowchart indicating process steps for embodiments of the present invention.

FIG. 9 is a flowchart 900 indicating process steps for embodiments of the present invention. In process step 950, traction is applied to the penis. In process step 952 light of NIR wavelengths is applied to the penis. Thus, embodiments provide a device where traction force and near-infrared light wavelengths are simultaneously applied to the penis. In process step 954, usage statistics are provided to an external computing device (e.g. smartphone). In process step 956, a check is made to see if a predetermined usage time has been exceeded. If not, the process returns periodically to process step 954 to send usage statistics. If the time is exceeded, the process proceeds to process step 958 to send a stop alert (as illustrated in FIG. 8B). The process may optionally continue to process step 960 of deactivating the light source.

In yet other embodiments, a plurality of LEDs may be applied to an interior of a penis pump. A penis pump is a known erectile dysfunction treatment. With disclosed embodiments, a plurality of LEDs may be disposed on a penis pump such that they provide light incident to the penis. This provides the aforementioned therapeutic benefits of the LEDs with the erectile dysfunction treatment provided by a penis pump.

As can now be appreciated, disclosed embodiments provide an improved traction device for extending a human penis. The apparatus of disclosed embodiments can be conveniently and discretely used for an improved technique for extending a human penis. This provides benefits of improved sexual health and increased confidence for men in a discrete and easy-to-use apparatus.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A traction apparatus for a penis, comprising:
a base section;
an arm section rotatably connected to the base section,
wherein the arm section includes a pivot ring that inserts into a slit in the base section, and
wherein the pivot ring comprises a conductive strip that provides electricity from the base section to the arm section;
a head section affixed to a distal end of the arm section via a magnetic power connector of the distal end of the arm section,
wherein the magnetic power connector provides power to the head section, and
wherein the magnetic power connector comprises a magnetic surface and a plurality of conductors that traverse the magnetic surface such that when a corresponding magnetic power connection is adjacent the magnetic power connector, the magnetic surface secures the magnetic power connection to the magnetic power connector and the plurality of conductors align with other conductors of the corresponding magnetic power connection to provide power to another section of the traction apparatus; and
a first light source affixed to the arm section, wherein the first light source is configured and is disposed to provide light with a wavelength ranging from 630 nanometers to 980 nanometers to the penis coinciding with an application of a traction force to the penis.

2. The traction apparatus of claim 1,
wherein the arm section comprises a first arm and a second arm, and
wherein the first arm comprises a first slide lock configured and disposed to extend the first arm, and
wherein the second arm comprises a second slide lock configured and disposed to extend the second arm.

3. The traction apparatus of claim 1,
wherein the head section comprises a second light source, and
wherein the second light source is configured and disposed to provide the light to the penis.

4. The traction apparatus of claim 3, wherein the first light source and second light source comprise a plurality of light emitting diodes.

5. The traction apparatus of claim 4, wherein the plurality of light emitting diodes that comprise the first light source and the second light source are configured in two rows.

6. The traction apparatus of claim 5,
wherein a first row of light emitting diodes from the two rows of light emitting diodes is configured to emit the light with a wavelength of 680 nanometers, and
wherein a second row of light emitting diodes from the two rows of light emitting diodes is configured to emit the light with a wavelength of 800 nanometers.

7. The traction apparatus of claim 3, wherein the second light source is configured to emit the light with the wavelength ranging from 630 nanometers to 980 nanometers.

8. The traction apparatus of claim 1,
wherein the arm section comprises an arm magnetic mount on a distal end of the arm section, and
wherein the head section comprises a head magnetic mount on an end of the head section.

9. A traction apparatus for a penis, comprising:
a base section;
an arm section rotatably connected to the base section,
wherein the arm section includes a pivot ring that inserts into a slit in the base section, and
wherein the pivot ring comprises a conductive strip that provides electricity from the base section to the arm section;

a head section affixed to a distal end of the arm section via a magnetic power connector of the distal end of the arm section, wherein the magnetic power connector provides power to the head section, and wherein the magnetic power connector comprises a magnetic surface and a plurality of conductors that traverse the magnetic surface such that when a corresponding magnetic power connection is adjacent the magnetic power connector, the magnetic surface secures the magnetic power connection to the magnetic power connector and the plurality of conductors align with other conductors of the corresponding magnetic power connection to provide power to another section of the traction apparatus;

a first light source affixed to the arm section, wherein the first light source is configured and is disposed to provide light with a wavelength ranging from 630 nanometers to 980 nanometers to the penis coinciding with an application of a traction force to the penis; and a controller coupled to the first light source, wherein the controller comprises:

a processor;

a communication interface coupled to the processor;

a memory coupled to the processor;

wherein the memory contains instructions, that when executed by the processor, perform the steps of:

recording usage time; and transmitting the recorded usage time via the communication interface.

10. The traction apparatus of claim 9, wherein the arm section comprises a first arm and a second arm, and wherein the first arm comprises a first slide lock configured and disposed to extend the first arm, and wherein the second arm comprises a second slide lock configured and disposed to extend the second arm.

11. The traction apparatus of claim 9, wherein the head section comprises a second light source, wherein the second light source is configured and disposed to provide light to the penis.

12. The traction apparatus of claim 11, wherein the first light source and second light source comprise a plurality of light emitting diodes.

13. The traction apparatus of claim 11, wherein the second light source is configured to emit the light with the wavelength ranging from 630 nanometers to 980 nanometers.

14. The traction apparatus of claim 9, wherein the arm section comprises an arm magnetic mount on a distal end of the arm section, and wherein the head section comprises a head magnetic mount on an end of the head section.

15. The traction apparatus of claim 14, wherein the arm magnetic mount and the head magnetic mount each comprise an electrical conductor.

\* \* \* \* \*